US011959067B2

(12) United States Patent
Guan

(10) Patent No.: US 11,959,067 B2
(45) Date of Patent: Apr. 16, 2024

(54) BIFIDOBACTERIUM LACTIS STRAIN FOR PREVENTING OR TREATING COLITIS AND METHOD FOR PREVENTING OR ALLEVIATING COLITIS

(71) Applicant: HARBIN SUNFLOWER PHARMACEUTICAL CO., LTD., Longjiang (CN)

(72) Inventor: Yanbin Guan, Longjiang (CN)

(73) Assignee: HARBIN SUNFLOWER PHARMACEUTICAL CO., LTD., Longjiang (CN)

(*) Notice: Subject to any disclaimer, the term of this patent is extended or adjusted under 35 U.S.C. 154(b) by 0 days.

(21) Appl. No.: 17/900,862

(22) Filed: Aug. 31, 2022

(65) Prior Publication Data
US 2023/0069454 A1    Mar. 2, 2023

(30) Foreign Application Priority Data

Sep. 1, 2021  (CN) .......................... 202111022649.X

(51) Int. Cl.
   *C12N 1/20*     (2006.01)
   *A61K 35/745*   (2015.01)
   *A61P 1/04*     (2006.01)
   *C12R 1/04*     (2006.01)

(52) U.S. Cl.
   CPC ............ *C12N 1/205* (2021.05); *A61K 35/745* (2013.01); *A61P 1/04* (2018.01); *C12R 2001/04* (2021.05)

(58) Field of Classification Search
   CPC ............................ C12N 1/205; A61K 35/745
   See application file for complete search history.

(56) References Cited

FOREIGN PATENT DOCUMENTS

CN          110893194 B  *  3/2020  .............. A61P 1/00

OTHER PUBLICATIONS

Wang et al. "Alleviation Effects of *Bifidobacterium animalis* subsp. *lactis* XLTG11 on Dextran Sulfate Sodium-Induced Colitis in Mice" Microorganisms 2021, 9, 2093, 15 pages (Year: 2021).*
Xu et al. "*Bifidobacterium animalis* subsp. *lactis* XLTG11 improves antibiotic-related diarrhea by alleviating inflammation, enhancing intestinal barrier function and regulating intestinal flora" Food Funct., 2022, 13, 6404-6418 (Year: 2022).*
Chassaing et al. "Dextran Sulfate Sodium (DSS)-Induced Colitis in Mice" Curr Protoc Immunol. ; 104: Unit-15.25, 16 pgs 2014 (Year: 2014).*
Mayo Clinic "Ulcerative colitis: Symptoms and causes" 2 pgs 1998-2023 (Year: 1998).*
Nagpal et al. "Human-origin probiotic cocktail increases short-chain fatty acid production via modulation of mice and human gut microbiome" SCIeNTIFIC Reports | (2018) 8:12649, 15 pgs (Year: 2018).*
Score results for SEQ ID No. 1 "Result 8" 3 pgs, search performed Apr. 2023 (Year: 2023).*
Xia et al. "Lactobacillus plantarum AR113 alleviates DSS-induced colitis by regulating the TLR4/MyD88/NF-κB pathway and gut microbiota composition" Journal of Functional Foods 67 (2020) 103854, 13 pages (Year: 2020).*
Janda et al. "16S rRNA Gene Sequencing for Bacterial Identification in the Diagnostic Laboratory: Pluses, Perils, and Pitfalls" Journal of Clinical Microbiology, Sep. 2007, p. 2761-2764 (Year: 2007).*
Cui et al. "The anti-inflammation effect of baicalin on experimental colitis through inhibiting TLR4/NF-κB pathway activation" International Immunopharmacology 23 (2014) 294-303 (Year: 2014).*
Lui et al. "NF-κB signaling in inflammation" Signal Transduction and Targeted Therapy (2017) 2, e17023; doi:10.1038/sigtrans.2017. 23 (Year: 2017).*
Morgane Rossi-Tamisier et al. "Cautionary tale of using 16S rRNA gene sequence similarity values in identification of human-associated bacterial species" International Journal of Systematic and Evolutionary Microbiology (2015), 65, 1929-1934 (Year: 2015).*
Ramya Srinivasan et al. "Use of 16S rRNA Gene for Identification of a Broad Range of Clinically Relevant Bacterial Pathogens" Plos One | DOI: 10.1371/journal.pone.0117617 Feb. 6, 2015, 22 pages (Year: 2015).*
Thea Van Rossum et al., "Diversity within species: interpreting strains in microbiomes", Nature Reviews Microbiology, Sep. 2020, pp. 491-506, vol. 18, No. 9.
Ma, Yan et al., "Alleviating effect of *Bifidobacterium animalis* subsp. *lactis* XLTG11 on ulcerative colitis induced by sodium dextran sulfate in mice", Dec. 23, 2021, Available at: https://kns.cnki.net/kcms/detail/11.2206.TS.20211222.1541.005.html, with English abstract, pp. 1-14.
Nana Wang et al., "Alleviation Effects of *Bifidobacterium animalis* subsp. *lactis* XLTG11 on Dextran Sulfate Sodium-Induced Colitis in Mice", Microorganisms, Oct. 3, 2021, pp. 1-15, vol. 9.

(Continued)

*Primary Examiner* — Thane Underdahl
(74) *Attorney, Agent, or Firm* — JCIPRNET

(57) ABSTRACT

The present disclosure provides a *Bifidobacterium lactis* (*B. lactis*) strain XLTG11 and a use thereof. The strain belongs to *Bifidobacterium lactis*. The *B. lactis* strain XLTG11 was deposited in the China General Microbiological Culture Collection Center (CGMCC) on Oct. 25, 2019, with a taxonomic name of *Bifidobacterium lactis* XLTG11 and an accession number of CGMCC No. 18738. The *B. lactis* strain XLTG11 provided by the present disclosure can regulate an inflammatory cytokine, improve an intestinal barrier function, and modulate an intestinal flora by inhibiting the activation of a TLR4/MYD88/NF-κB signaling pathway, thereby alleviating dextran sulfate sodium (DSS)-induced colitis. In addition, the *B. lactis* strain XLTG11 has an immune-enhancing effect on a cyclophosphamide (CTX)-induced mouse immunosuppression model.

9 Claims, 12 Drawing Sheets
Specification includes a Sequence Listing.

(56) References Cited

OTHER PUBLICATIONS

Baofeng Xu et al., "*Bifidobacterium animalis* subsp. *lactis* XLTG11 improves antibiotic-related diarrhea by alleviating inflammation, enhancing intestinal barrier function and regulating intestinal flora", Food & Function, Apr. 22, 2022, pp. 6404-6418, vol. 13.

Ma, Weiwei et al., "Effects of Bifidobacterium lactis XLTG11 on immune function in mice", Dec. 8, 2021, Available at: https://doi.org/10.13995/j.cnki.11-1802/ts.029673, with English abstract, pp. 1-8.

Pediaa, "What is the Difference Between Strain and Species", Apr. 1, 2020, Available at: https://pediaa.com/what-is-the-difference-between-strain-and-species/, pp. 1-7.

Li, Wenwen et al., "Bifidobacterium lactis XLTG11 Alleviates Cyclophosphamide-induced Immunosuppression in Mice", Modern Food Science and Technology, Dec. 6, 2021, pp. 10-16, vol. 38, No. 8.

\* cited by examiner

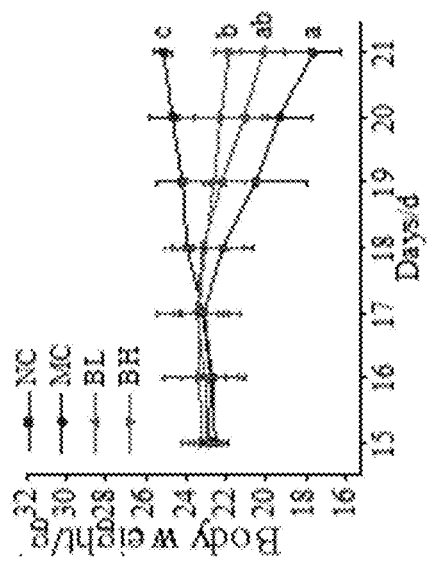
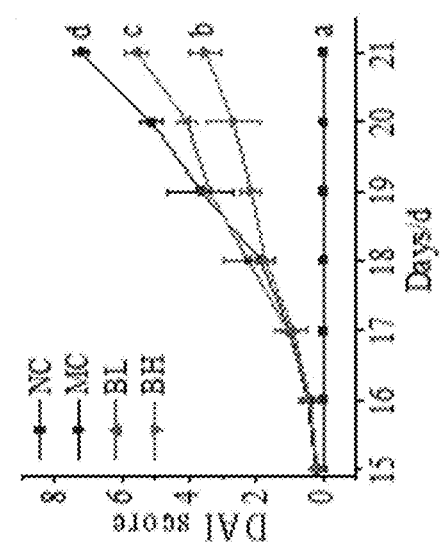
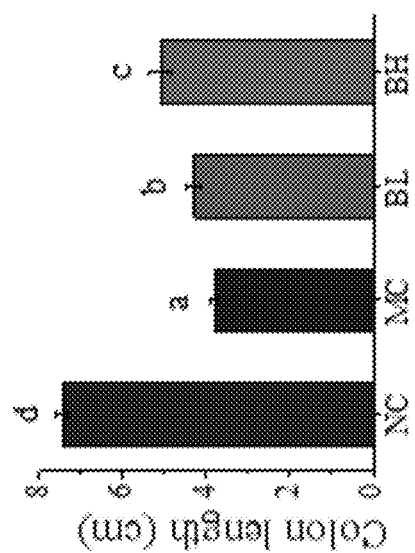
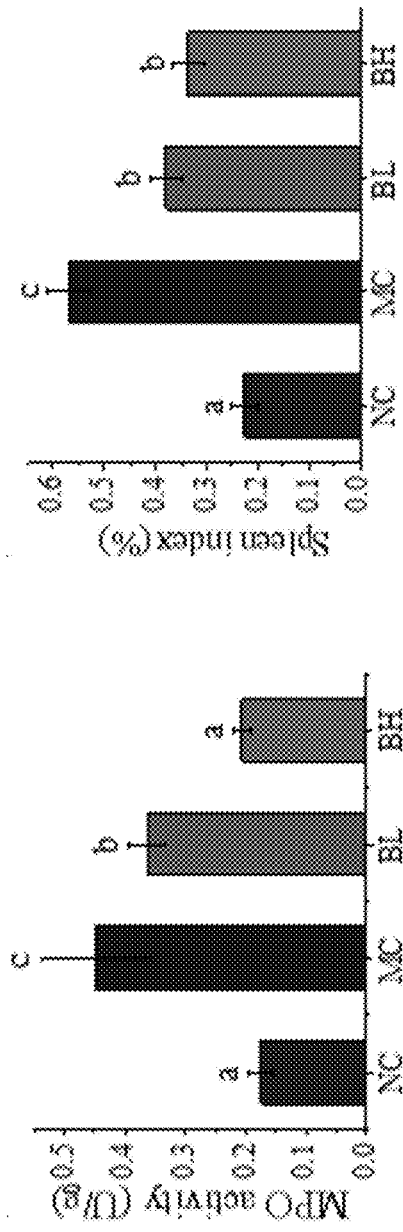
FIG. 1A
FIG. 1B
FIG. 1C
FIG. 1D
FIG. 1E

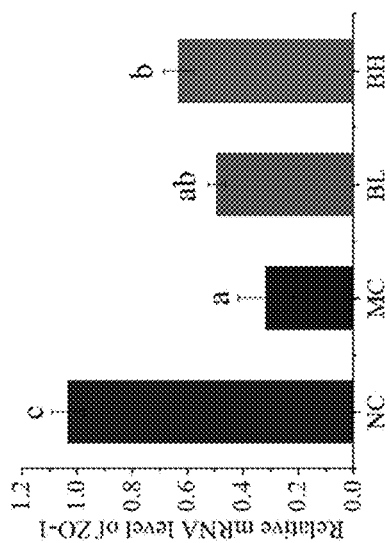
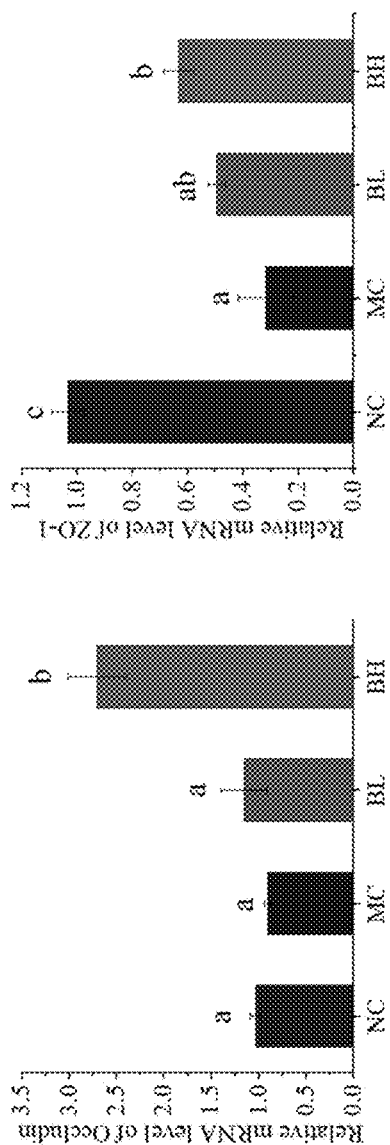
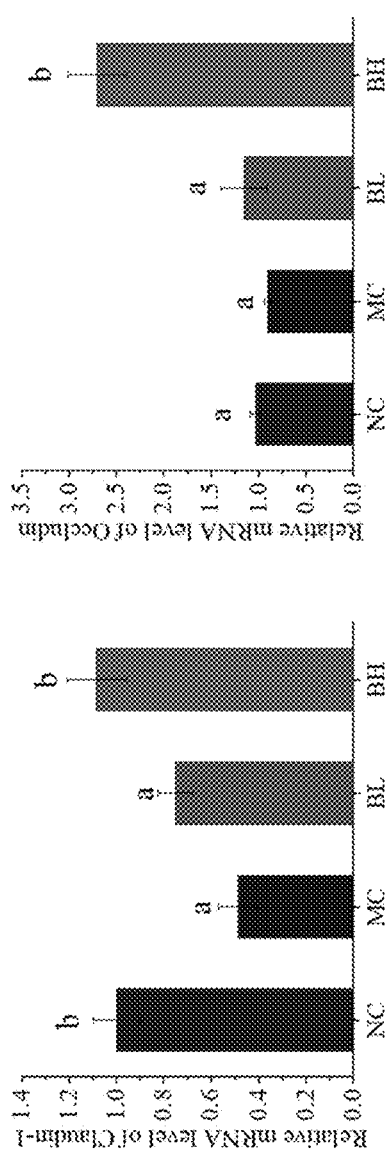
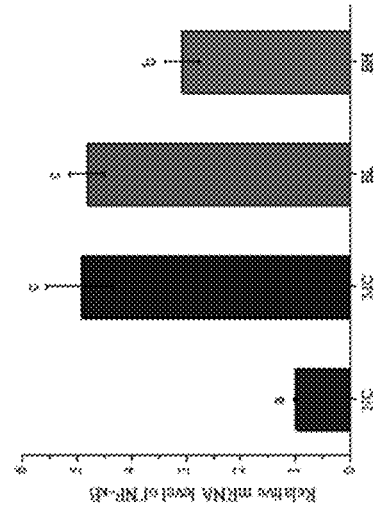
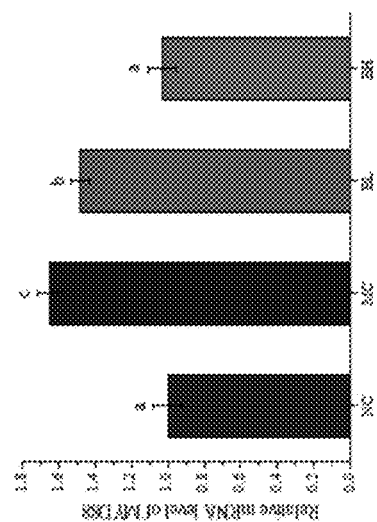
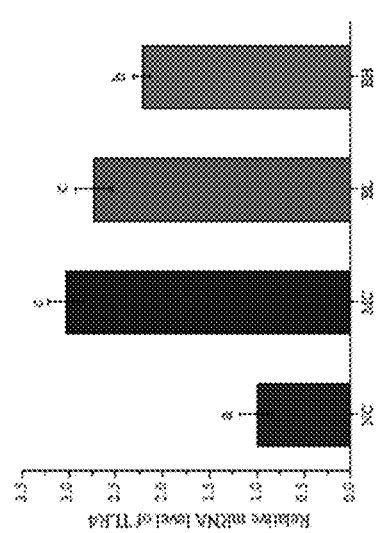

SEQUENCE LISTING

```
Sequence total quantity: 1
SEQ ID NO: 1            moltype = DNA  length = 1379
FEATURE                 Location/Qualifiers
source                  1..1379
                        mol_type = genomic DNA
                        note = 16S rDNA sequence of Bifidobacterium lactis strain
                        XLTG11
                        organism = unidentified
SEQUENCE: 1
acgggatccc tggcagcttg ctgtcgggt gagagtggcg aacgggtgag taatgcgtga   60
ccaacctgcc ctgtgcaccg gaatagctcc tggaaacggg tggtaatacc ggatgctccg  120
ctccatcgca tggtggggtg ggaaatgctt ttgcggcatg ggatgggggtc gcgtcctatc  180
agcttgttgg cggggtgatg gcccaccaag gcgttgacgg gtagccggcc tgagagggtg  240
accggccaca ttgggactga gatacggccc agactcctac gggaggcagc agtggggaat  300
attgcacaat gggcgcaagc ctgatgcagc gacgccgcgt gcgggatgga ggccttcggg  360
ttgtaaaccg ctttgttca agggcaaggc acggttcgg ccgtgttgag tggattgttc   420
gaataagcac cggctaacta cgtgccagca gccgcggtaa tacgtagggt gcgagcgtta  480
tccggattta ttgggcgtaa agggctcgta ggcggttcgt cgcgtccggt gtgaaagtcc  540
atcgcctaac ggtggatctg cgccgggtac gggcgggctg gagtgcggta ggggagactg  600
gaattcccgg tgtaacggtg gaatgtgtag atatcgggaa gaacaccaat ggcgaaggca  660
ggtctctggg ccgtcactga cgctgaggag cgaaagcgtg gggagcgaac aggattagat  720
accctggtag tccacgccgt aaacggtgga tgctggatgt ggggcccttt ccacgggtcc  780
cgtgtcggag ccaacgcgtt aagcatccccg cctggggagt acggccgcaa ggctaaaact  840
caaagaaatt gacgggggcc cgcacaagcg gcggagcatg cggattaatt cgatgcaacg  900
cgaagaacct tacctgggct tgacatgtgc cggatcgccg tggagacacg gtttcccttc  960
ggggccggtt cacaggtggt gcatggtcgt cgtcagctcg tgtcgtgaga tgttgggtta 1020
agtcccgcaa cgagcgcaac cctcgccgca tgttgccagc gggtgatgcc gggaactcat 1080
gtgggaccgc cggggtcaac tcggaggaag gtggggatga cgtcagatca tcatgcccct 1140
tacgtccagg gcttcacgca tgctacaatg gccggtacaa cgcggtgcga cacggtgacg 1200
tggggcggat cgctgaaaac cggtctcagt tcggatcgca gtctgcaact cgactgcgtg 1260
aaggcggagt cgctagtaat gcggatcag caacgccgcg gtgaatgcgt tcccgggcct 1320
tgtacacacc gcccgtcaag tcatgaaagt gggtagcacc cgaagccggt ggcccgacc  1379
```

BIFIDOBACTERIUM LACTIS STRAIN FOR PREVENTING OR TREATING COLITIS AND METHOD FOR PREVENTING OR ALLEVIATING COLITIS

CROSS-REFERENCE TO RELATED APPLICATION

This application claims the priority benefit of China application serial no. 202111022649.X, filed on Sep. 1, 2021. The entirety of the above-mentioned patent application is hereby incorporated by reference herein and made a part of this specification.

TECHNICAL FIELD

The present disclosure relates to a *Bifidobacterium lactis* (*B. lactis*) strain and a use thereof, and belongs to the field of biotechnology.

BACKGROUND

Inflammatory bowel disease (IBD) is a chronic and relapsing autoimmune disease, including ulcerative colitis (UC) and Crohn's disease (CD). IBD has the highest incidence in Western countries. In recent years, the incidence of IBD has risen sharply in Asian, African, and South American countries with the industrial development. The specific pathogenesis of IBD is unclear, but increasing data suggest that genetic susceptibility, abnormal immune responses, impaired intestinal barrier, and intestinal flora imbalance play important roles in the development of IBD. Traditional therapeutic drugs such as aminosalicylates, immunosuppressants, and biological drugs often lead to severe side effects such as headaches, nausea, and infections, and thus it is important to develop a safe and effective treatment for alleviating IBD symptoms.

Intestinal microorganisms play a crucial role in human energy metabolism and immune processes, and increasing evidence shows that the intestinal microbial dysbiosis is associated with some human diseases, such as obesity, allergy, IBD, and type 2 diabetes. A composition of an intestinal flora is closely related to an immune system of a host. Firmicutes and Bacteroidetes are two most abundant phyla among intestinal microorganisms and are closely associated with the intestinal health. Studies have shown that, in an intestinal tract of an IBD patient, a relative abundance of Firmicutes increases, while a relative abundance of Bacteroidetes decreases. In addition, studies have shown that a relative abundance of potential pathogens (*Escherichia coli* (*E. coli*) and Proteobacteria) in a UC patient increases compared with a healthy subject. The pathogens invade intestinal epithelial cells (IECs) to stimulate inflammation, disrupt the integrity of an intestinal epithelial barrier, and trigger an intestinal inflammatory response. Therefore, intestinal microorganisms may be an important potential target for UC treatment.

Probiotics are a class of living microorganisms that colonize in the human intestinal tract, and are beneficial to the intestinal health, which especially include *Lactobacillus* and *Bifidobacterium* that interfere with intestinal inflammation. *Bifidobacterium* plays a specific role in reducing the abundance and colonization of opportunistic pathogens, maintaining the microbial homeostasis of a host, protecting the integrity of an intestinal mucosal barrier, and regulating the intestinal inflammation. Previous studies have shown that *Bifidobacterium breve* (*B. breve*) can effectively alleviate dextran sulfate sodium (DSS)-induced colitis by inhibiting inflammatory cytokines, enhancing intestinal epithelial barrier functions, and modulating intestinal floras. Din et al. found that the *Bifidobacterium* strain ATCC29521 can alleviate DSS-induced UC by regulating the miRNA-associated tight junction protein (TJP) and NF-κB pathway and improving the microbial dysbiosis to some extent. However, it is rarely reported that *B. lactis* can improve colitis and enhance immunity.

SUMMARY

In the present disclosure, a new *B. lactis* strain XLTG11 is screened out from intestinal tracts of healthy children. The *B. lactis* strain XLTG11 belongs to *Bifidobacterium lactis*, and was deposited in the China General Microbiological Culture Collection Center (CGMCC) on Oct. 25, 2019, with a taxonomic name of *Bifidobacterium lactis* XLTG11 and an accession number of CGMCC No. 18738; and the China General Microbiological Culture Collection Center (CGMCC) is located at the Institute of Microbiology, Chinese Academy of Sciences, No. 1, West Beichen Road, Chaoyang District, Beijing, China.

The *B. lactis* strain XLTG11 of the present disclosure has the following biological characteristics: Gram-positive, anaerobic, non-motile, non-spore-forming, and smooth and gibbous colonies with intact edges, and white creamy appearance.

After the *B. lactis* strain XLTG11 is digested in an artificial gastric fluid with pH 2.5 for 3 h, a survival rate of the *B. lactis* strain XLTG11 is 75.01%, and after the *B. lactis* strain XLTG11 is further digested in an artificial digestive fluid with pH 8.0 for 11 h, a survival rate of the *B. lactis* strain XLTG11 is as high as 89.75%, indicating that the *B. lactis* strain XLTG11 has a high tolerance to a gastrointestinal digestive fluid, and can enter a human intestinal tract in a living state to exert a health effect.

The *B. lactis* strain XLTG11 of the present disclosure can alleviate DSS-induced colitis in mice, significantly alleviate the body weight loss, disease activity index (DAI) score, and colon shortening in mice, and significantly reduce the myeloperoxidase (MPO) activity, spleen weight, and colon tissue damage degree in a dose-dependent manner.

The *B. lactis* strain XLTG11 can significantly reduce a pro-inflammatory cytokine (TNF-α, IL-1β, and IL-6) level and increase an anti-inflammatory cytokine IL-10 level, and the high-dose *B. lactis* strain XLTG11 can significantly up-regulate the expression of TJPs (claudin-1, occludin, and ZO-1) and inhibit the activation of a TLR4/MYD88/NF-κB signaling pathway.

The supplementation with the *B. lactis* strain XLTG11 increases the diversity of the intestinal flora and regulates the DSS-induced intestinal flora disturbance.

The *B. lactis* strain XLTG11 can regulate an inflammatory cytokine, improve an intestinal barrier function, and modulate an intestinal flora by inhibiting the activation of a TLR4/MYD88/NF-κB signaling pathway, thereby alleviating DSS-induced colitis.

The *B. lactis* strain XLTG11 can increase a swelling degree of toes in mice, increase a thymus index and the levels of cytokines IL-2 and TNF-α in CTX mice, and enhance a lymphocyte function to play an immunomodulatory effect.

The *B. lactis* strain XLTG11 can enhance an immune function of the body. The *B. lactis* strain XLTG11 is orally gavaged to a cyclophosphamide (CTX)-induced immunocompromised mouse model to investigate the influence of the *B. lactis* strain XLTG11 on the thymus index and spleen index, cellular immune functions, pathological changes in the small intestinal mucosal tissues, and inflammatory cytokines.

Further, the present disclosure provides a product for preventing and/or treating colitis or enhancing an immunomodulatory function. The product is preferably a drug, a food, or the like, and the product includes the *B. lactis* strain XLTG11 described above. When the product is used, the *B. lactis* strain XLTG11 is included at a dosage of $1 \times 10^6$ cfu to $1 \times 10^9$ cfu.

The present disclosure further provides a microbial agent including the *B. lactis* strain XLTG11 described above and a preparation method thereof. The preparation method of the microbial agent includes: anaerobically cultivating the *B. lactis* strain XLTG11 for 18 h at 37° C. in a modified MRS medium supplemented with 0.05% cysteine hydrochloride, passaging and cultivating, collecting cells of the *B. lactis* strain XLTG11 through a centrifugation, washing the cells 3 times with sterile phosphate buffered saline (PBS), and resuspending the cells in PBS at concentrations of $1 \times 10^7$ CFU/mL and $1 \times 10^8$ CFU/mL.

The *B. lactis* strain XLTG11 and the microbial agent in the present disclosure can each be used in combination with other probiotics to jointly prevent and/or treat colitis or enhance an immunomodulatory function. The colitis is preferably UC.

BRIEF DESCRIPTION OF THE DRAWINGS

FIGS. 1A to 1E show the influence of *B. lactis* strain XLTG11 on the symptoms of DSS-induced colitis in mice, where FIG. 1A: body weight, FIG. 1B: DAI score, FIG. 1C: colon length, FIG. 1D: MPO activity, and FIG. 1E: spleen index; NC: normal control group, MC: model control group, BL: low-dose *B. lactis* strain XLTG11 group, and BH: high-dose *B. lactis* strain XLTG11 group; all data are presented as mean±standard deviation (SD); and different letters indicate statistical differences among the groups ($P<0.05$).

FIG. 2A: histological images, and FIG. 2B: histological scores; NC: normal control group, MC: model control group, BL: low-dose *B. lactis* strain XLTG11 group, and BH: high-dose *B. lactis* strain XLTG11 group; all data are presented as mean±SD; and different letters indicate statistical differences among the groups ($P<0.05$).

FIG. 3A: IL-10, FIG. 3B: IL-1β, FIG. 3C: TNF-α, and FIG. 3D: IL-6; NC: normal control group, MC: model control group, BL: low-dose *B. lactis* strain XLTG11 group, and BH: high-dose *B. lactis* strain XLTG11 group; all data are presented as mean±SD; and different letters indicate statistical differences among the groups ($P<0.05$).

FIGS. 4A to 4C show the influence of *B. lactis* strain XLTG11 on the mRNA expression of claudin-1 (FIG. 4A), occlusion ((FIG. 4B), and ZO-1 ((FIG. 4C) in colon tissues that is determined by quantitative real-time polymerase chain reaction (qRT-PCR), NC: normal control group, MC: model control group, BL: low-dose *B. lactis* strain XLTG11 group, and BH: high-dose *B. lactis* strain XLTG11 group; all data are presented as mean±SD; and different letters indicate statistical differences among the groups ($P<0.05$).

FIGS. 5A to 5C show the influence of *B. lactis* strain XLTG11 on the mRNA expression of TLR4 (FIG. 5A), MYD88 (FIG. 5B), and NF-κB (FIG. 5C) in colon tissues that is determined by qRT-PCR, NC: normal control group, MC: model control group, BL: low-dose *B. lactis* strain XLTG11 group, and BH: high-dose *B. lactis* strain XLTG11 group; all data are presented as mean±SD; and different letters indicate statistical differences among the groups ($P<0.05$).

FIG. 6A: number of observed species, FIG. 6B: Simpson index, FIG. 6C: composition of the intestinal flora at a phylum level, and FIG. 6D: composition of the intestinal flora at a genus level; and NC: normal control group, MC: model control group, BL: low-dose *B. lactis* strain XLTG11 group, and BH: high-dose *B. lactis* strain XLTG11 group.

DETAILED DESCRIPTION OF THE EMBODIMENTS

Figure 2B:
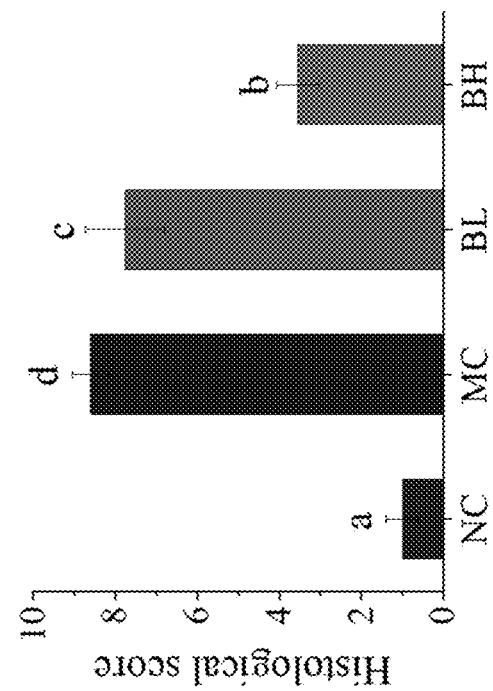
FIGS. 2A and 2B show the influence of *B. lactis* strain XLTG11 on the histopathological analysis of colon tissues, where

Example 1 Screening and Identification of *B. lactis* Strain

A strain was isolated from intestinal tracts of healthy children and identified by 16s rRNA full-length sequencing (SEQ ID NO: 1) and mass spectrometry (MS). The strain belongs to *Bifidobacterium lactis*, and the strain was deposited in the China General Microbiological Culture Collection Center (CGMCC) on Oct. 25, 2019, with a taxonomic name of *Bifidobacterium lactis* XLTG11 and an accession number of CGMCC No. 18738; and the China General Microbiological Culture Collection Center (CGMCC) is located at the Institute of Microbiology, Chinese Academy of Sciences, No. 1, West Beichen Road, Chaoyang District, Beijing, China.

The *B. lactis* strain XLTG11 has the following biological characteristics: Gram-positive, anaerobic, non-motile, non-spore-forming, and smooth and gibbous colonies with intact edges, and white creamy appearance.

The tolerance of the *B. lactis* strain XLTG11 to artificial gastric and intestinal fluids was tested. After the *B. lactis* strain XLTG11 was digested in an artificial gastric fluid with pH 2.5 for 3 h, a survival rate of the *B. lactis* strain was 75.01%, and after the *B. lactis* strain XLTG11 was further digested in an artificial digestive fluid with pH 8.0 for 11 h, a survival rate of the *B. lactis* strain was as high as 89.75%, indicating that the B. lactis strain has high tolerance to a gastrointestinal digestive fluid, and can enter a human intestinal tract in a living state to exert a health effect.

Example 2 Preparation of a Bacterial Suspension

The strain was anaerobically cultivated for 18 h at 37° C. in a modified MRS medium with 0.05% cysteine hydrochloride (China Qingdao Hope Biological Co., Ltd., HB0384-5), and passaged twice before the experiment. Cells of the B. lactis strain XLTG11 were collected through centrifugation at 6,000×g and 4° C. for 10 min, washed three times with sterile PBS, and resuspended in PBS at concentrations of $1\times10^7$ CFU/mL and $1\times10^8$ CFU/mL.

Example 3 Influence of B. lactis Strain XLTG11 on the Symptoms of DSS-Induced Colitis 8-week-old specific pathogen-free (SPF) C57BL/6 male mice were purchased from the Beijing Vital River Laboratory Animal Technology Co., Ltd. Before the experiment, all animals were raised for one week at a temperature of 23±2° C. and a humidity of 50%±10% with a 12 h light-dark cycle for acclimatisation. The mice were randomly divided into four groups: normal control group (NC), model control group (MC), low-dose B. lactis strain XLTG11 group (BL), and high-dose B. lactis strain XLTG11 group (BH). During the experiment, the BL and BH groups were orally administered with low-dose B. lactis strain XLTG11 ($1\times10^7$ CFU/d) and high-dose B. lactis strain XLTG11 ($1\times10^8$ CFU/d) once a day, respectively. The NC and MC groups were each injected with 200 μL of PBS once a day at the same raising frequency. From day 15 to day 21, all mice except mice in the NC group drank 2.5% DSS-containing drinking water to induce colitis. During DSS treatment, a body weight was measured for all mice every day, and a DAI score was recorded based on the body weight loss, stool consistency, and total blood volume. After the experiment was completed, the mice were fasted for 12 h and then anesthetized and sacrificed. Blood was collected from eyeballs of all mice and centrifuged at 4° C. and 3,500 rpm for 15 min to obtain serum, and the serum was stored at −80° C. A colon content was collected under sterile conditions and then stored at −80° C. for intestinal flora analysis. A colon was collected and the colon length was measured, and the colon was rinsed with normal saline (NS). The excised colon tissue was immediately fixed in 4% paraformaldehyde (PFA) for histopathological analysis, and the remaining tissue was stored at −80° C. for qRT-PCR. A spleen was collected and weighed, and a spleen index was calculated as follows: organ weight (g)/body weight (g)×100.

Measured body weights during DSS induction were shown in FIG. 1A, and it can be seen from the figure that a body weight of mice in the control group increased steadily; and body weights of mice in the other groups showed a downward trend from day 17 to the end of the experiment, where the downward trends in the low-dose and high-dose treatment groups were alleviated to some extent. DAI score changes were shown in FIG. 1B, and it can be seen from the figure that a DAI score of the control group remained at 0; a DAI score of the model group showed a rapid upward trend compared with the control group; and DAI score increments in the low-dose and high-dose groups were significantly smaller than that in the model group. The colon lengths of mice in the four groups were shown in FIG. 1C, and it can be seen from the figure that, compared with the control group, a colon length of the model group was significantly reduced (P<0.05); and after the microbial intervention, the DSS-induced colon shortening symptom was significantly alleviated (P<0.05). As shown in FIG. 1D, compared with the control group, the MPO activity of mice in the model group was significantly increased (P<0.05); and compared with the model group, the MPO activities of mice in the low-dose and high-dose groups were significantly decreased (P<0.05) in a dose-dependent manner, and there was no statistically-significant difference between the control group and the high-dose group (P>0.05). The spleen index of each treatment group was shown in FIG. 1E, and it can be seen from the figure that the spleen index of mice in the model group was significantly higher than the spleen index of mice in the control group (P<0.05), and the administration of the microorganism at the two doses alleviated these changes. The above results show that the B. lactis strain XLTG11 can effectively alleviate the symptoms of DSS-induced colitis.

Example 4 Influence of B. lactis Strain XLTG11 on the Histopathological Analysis of Colon Tissues A distal colon was fixed with 4% PFA for 48 h, embedded in paraffin, and sectioned to obtain 5 μm sections. The sections were dewaxed with xylene, then stained with hematoxylin-eosin (HE), and observed (a histological score was calculated by a method with reference to Tan, Y. et. al., The American journal of the medical sciences 2018, 355, 377-386; and Zhao, H. W. et. al., World journal of gastroenterology 2017, 23, 999-1009).

Figure 2A:
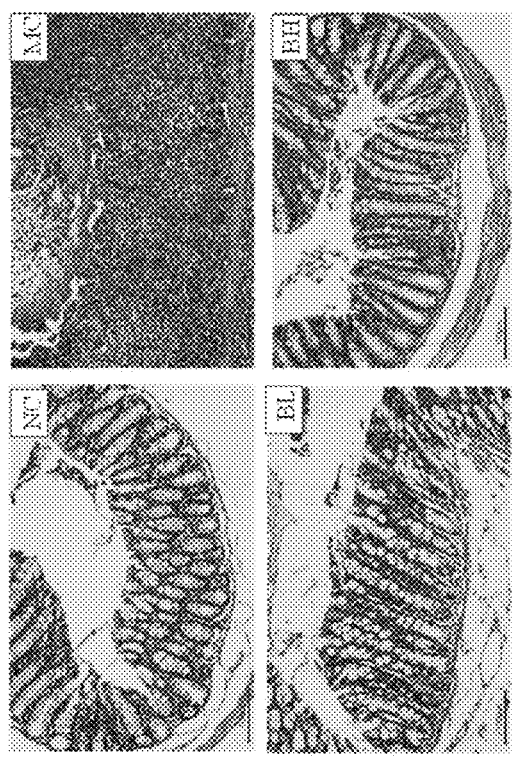
Figure 3A:
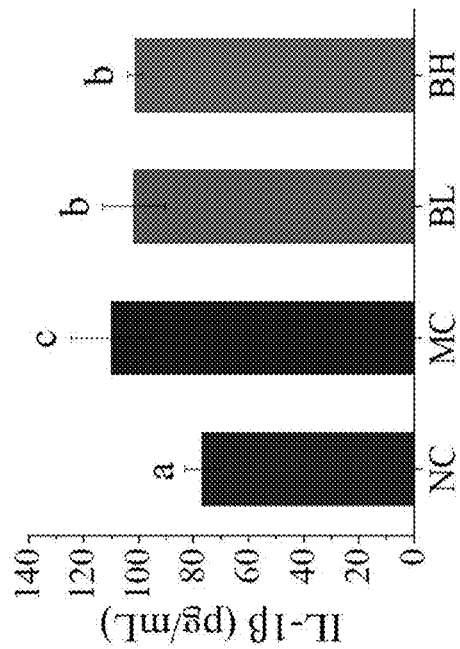
FIGS. 3A to 3D show the influence of *B. lactis* strain XLTG11 on inflammatory cytokines, where
Figure 3B:
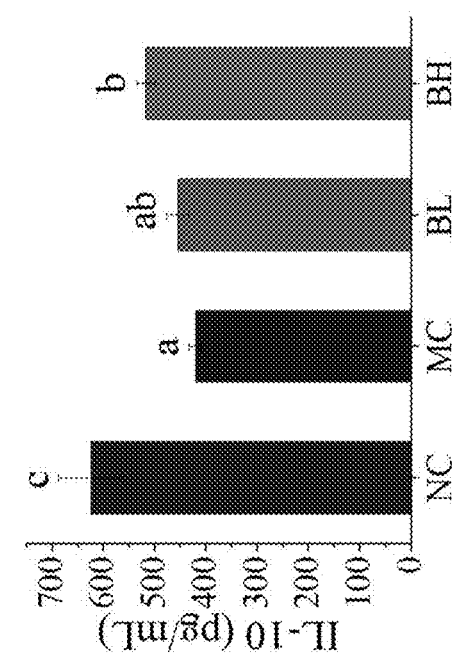
Figure 3C:
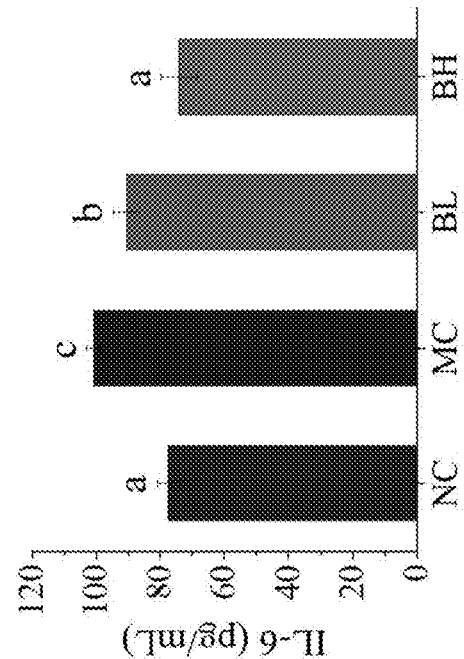
Figure 3D:
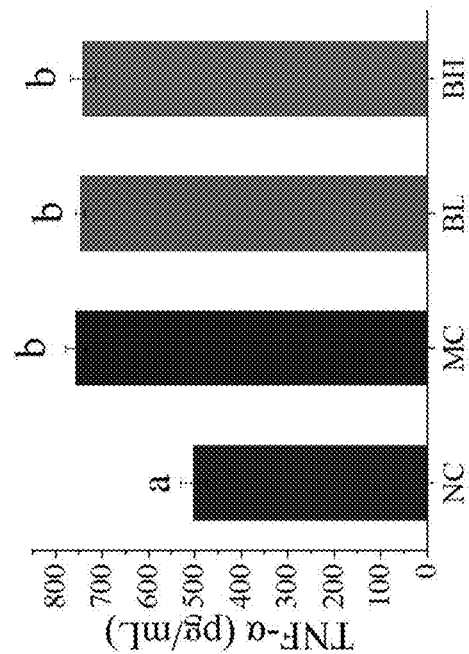

Histological changes of colons of mice in each treatment group were shown in FIG. 2A, and it can be seen from the figure that, in a colon tissue of mice in the control group, intact goblet cells and epithelial tissues were observed; and in a colon tissue of mice in the model group, the crypt structure and goblet cells disappeared and the inflammatory cell infiltration was observed. After the treatment with the B. lactis strain XLTG11, the structural damage to the colon tissue was improved in mice of the low-dose and high-dose groups, and the inflammatory cell infiltration was reduced. In addition, as shown in FIG. 2B, the two B. lactis doses both significantly reduced a DSS-induced histological score compared with the model group (P<0.05), and especially the high-dose group showed a stronger ability to reduce a pathological score than the low-dose group. These results show that the high-dose B. lactis strain XLTG11 can significantly improve the DSS-induced histomorphological change and decrease the histological score.

Example 5 Influence of B. lactis Strain XLTG11 on the Inflammatory Cytokines, the mRNA Expression of Claudin-1, Occludin, and ZO-1, and the TLR4/MYD88/NF-κB Signaling Pathway Colon tissues of mice in different treatment groups were each weighed, ground with a prepared reagent as a homogenization medium in a weight-to-volume ratio of 1:19, and tested for MPO. According to instructions, an ELISA kit (Quanzhou Kenuodi Bio-Technology Co., Ltd., Quanzhou, China) was used to detect the levels of interleukins IL-1β, IL-10, and IL-6 and tumor necrosis factor TNF-α in serum.

The levels of inflammatory cytokines in serum of mice in each treatment group were shown in FIGS. 3A to 3D, and it can be seen from the figure that the levels of proinflammatory cytokines (IL-1β, TNF-α, and IL-6) in serum of mice in the model group were significantly higher than that in the control group. The levels of IL-1β and IL-6 in serum of mice treated with *B. lactis* at the two doses were lower than that in the model group (P<0.05); there was no significant difference in the serum IL-6 level between mice in the high-dose group and mice in the control group (P>0.05); a serum IL-10 level in the DC group was significantly lower than that in the control group (P<0.05); and the high-dose *B. lactis* could significantly reverse the IL-10 level (P<0.05), but the low-dose group and the model group showed no significant changes (P>0.05). The above data show that, compared with the low-dose group, the administration of high-dose *B. lactis* strain XLTG11 can effectively inhibit the DSS-induced inflammatory symptoms.

The mRNA expression levels of colonic TJPs (claudin-1, occludin, and ZO-1) were shown in FIGS. 4A to 4C, and it can be seen from the figure that, compared with the control group, the expression levels of claudin-1 and ZO-1 in the model group were significantly decreased (p<0.05), indicating that the epithelial integrity was damaged. The mRNA expression levels of claudin-1 and ZO-1 were significantly increased in the high-dose group (P<0.05) compared with the model group, and there were significant changes in the low-dose group and the model group (P>0.05). In addition, the mRNA expression level of occludin-1 in the model group was not significantly different from that in the control group (P>0.05). It should be noted that the expression level of occludin-1 in the high-dose group receiving high-dose *B. lactis* strain XLTG11 was significantly higher than that in the model group. These results show that the administration of high-dose *B. lactis* strain XLTG11 can alleviate DSS-induced impairment to intestinal barrier functions.

In order to investigate whether the TLR4/MYD88/NF-κB signaling pathway plays an important role in an anti-inflammatory mechanism of *B. lactis* strain XLTG11, the mRNA expression levels of related genes were determined. The results were shown in FIGS. 5A to 5C. Compared with the control group, the DSS administration significantly increased the mRNA expression levels of TLR4, MYD88, and NF-κB (P<0.05). In contrast, the TLR4 and NF-κB gene expression was significantly down-regulated in the high-dose group (P<0.05), but there was no significant difference between the low-dose group and the model group (P>0.05). In addition, compared with the model group, the two doses of *B. lactis* strain XLTG11 significantly down-regulated the mRNA expression of MYD88 (P<0.05), and especially, the mRNA expression level in the high-dose group treated with *B. lactis* strain XLTG11 was similar to that in the NC group (P>0.05). The results show that the high-dose *B. lactis* strain XLTG11 can exert an anti-inflammatory function by inhibiting the activation of the TLR4/MYD88/NF-κB signaling pathway.

Example 6 Influence of *B. lactis* Strain XLTG11 on the Structure and Composition of an Intestinal Flora Relative mRNA levels of TJP genes (claudin-1, occlusion, and ZO-1) and TLR4 signaling pathway-associated genes (TLR4, MYD88, and NF-κB) were detected through qRT-PCR, with a GAPDH gene as an internal reference gene. Colonic total RNA was extracted with RNAiso Plus (Takara Biotechnology, Dalian, China) and quantified with a 2000C ultra-micro ultraviolet (UV) spectrophotometer (Thermo Fisher Scientific Inc., USA), and the extracted RNA was subjected to reverse transcription with reference to a Transcriptor First Strand cDNA Synthesis Kit RNA kit (Roche, Germany, 04897030001). qRT-PCR was conducted according to the instructions on the Bio-Rad CFX96 real-time PCR system (Bio-Rad, Foster City, CA, USA), the on-line detection was conducted with reference to the instructions of a kit Stormstar SybrGreen qPCR Master Mix (DBI Bioscience, Germany, DBI-2143), and data were analyzed by the 2-ΔΔCt method.

The flora DNA was extracted from colons of mice in each group (n=3) with a kit (Omega Bio-Tek, Norcross, GA, USA). PCR amplification was conducted on V3 and V4 regions of bacterial 16S rDNA with primers 338F and 806R: (5'-ACTCCTACGGGAGGCAGCAG-3') (forward primer) and (5'-GGACTACHVGGGTWTCTAAT-3') (reverse primer). The resulting PCR products were purified with an AxyPrep DNA Gel Extraction Kit (Axygen Biosciences, Union City, CA, USA) and quantified with a Qubit 2.0 fluorometer (Life Technologies, Carlsbad, CA, USA).

Sequencing was conducted on the IlluminaMiseq platform (Illumina Inc., San Diego, CA, USA). The raw data were merged with Flash (version 1.2.11) software and filtered by QIIME (V1.9.1) to collect high-quality labels. Valid labels were clustered by UCLUST (version 1.2.22) with a similarity ≥97% OTU [25]. Operational taxonomic units (OTUs) were analyzed by PyNAST software (version 1.2) based on the Greengenes database and the taxonomic information was annotated at the phylum and genus levels.

All data were analyzed with SPSS 22.0 software and expressed as mean±SD. A statistical difference was determined using one-way analysis of variance (ANOVA), and then the Duncan's multiple range test (DMRT) was conducted. A relationship between a dominant intestinal flora and UC-associated symptoms was evaluated by a Spearman correlation coefficient, and P<0.05 indicated that there was a statistically-significant difference.

Figures 6A, 6B:
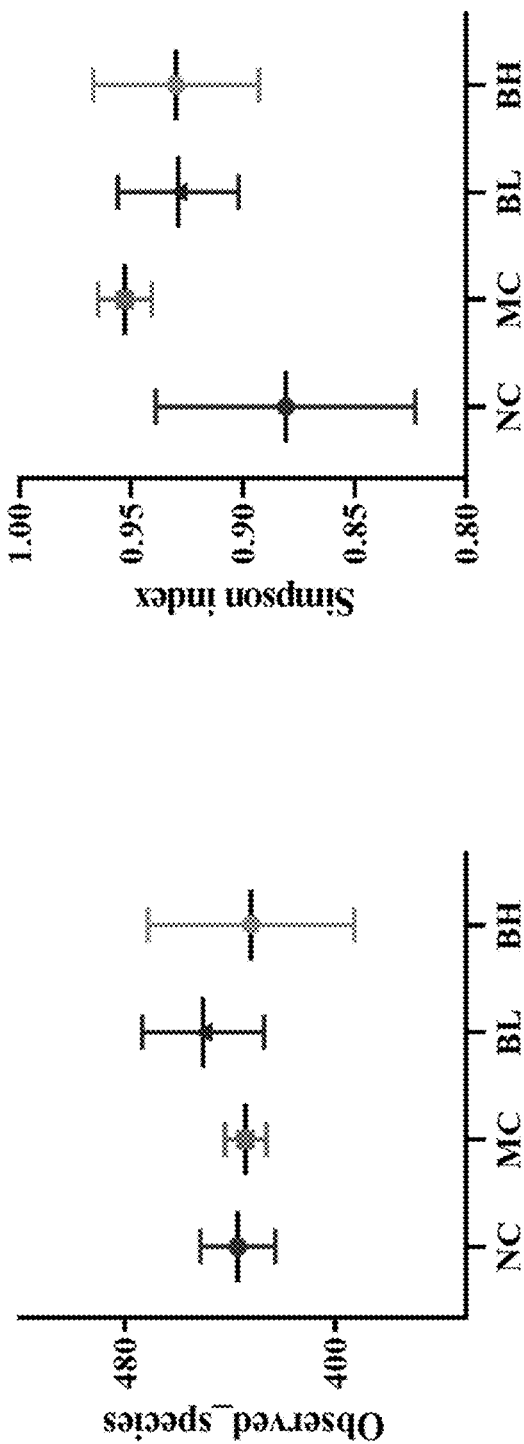
FIGS. 6A to 6D show the influence of *B. lactis* strain XLTG11 on the structure and composition of an intestinal flora, where

In this study, the V3 and V4 hypervariable regions of the 16S rDNA gene were sequenced, and the intestinal floras in colonic contents of different groups were analyzed. As shown in FIG. 6A and FIG. 6B, the number of observed species of mice in the model group was smaller than that in the control group, and the Simpson index of mice in the model group was higher than that in the control group, indicating that the DSS intake led to a decrease in microbial diversity, and the administration of *B. lactis* strain XLTG11 alleviated these changes to some extent.

Figure 6C:
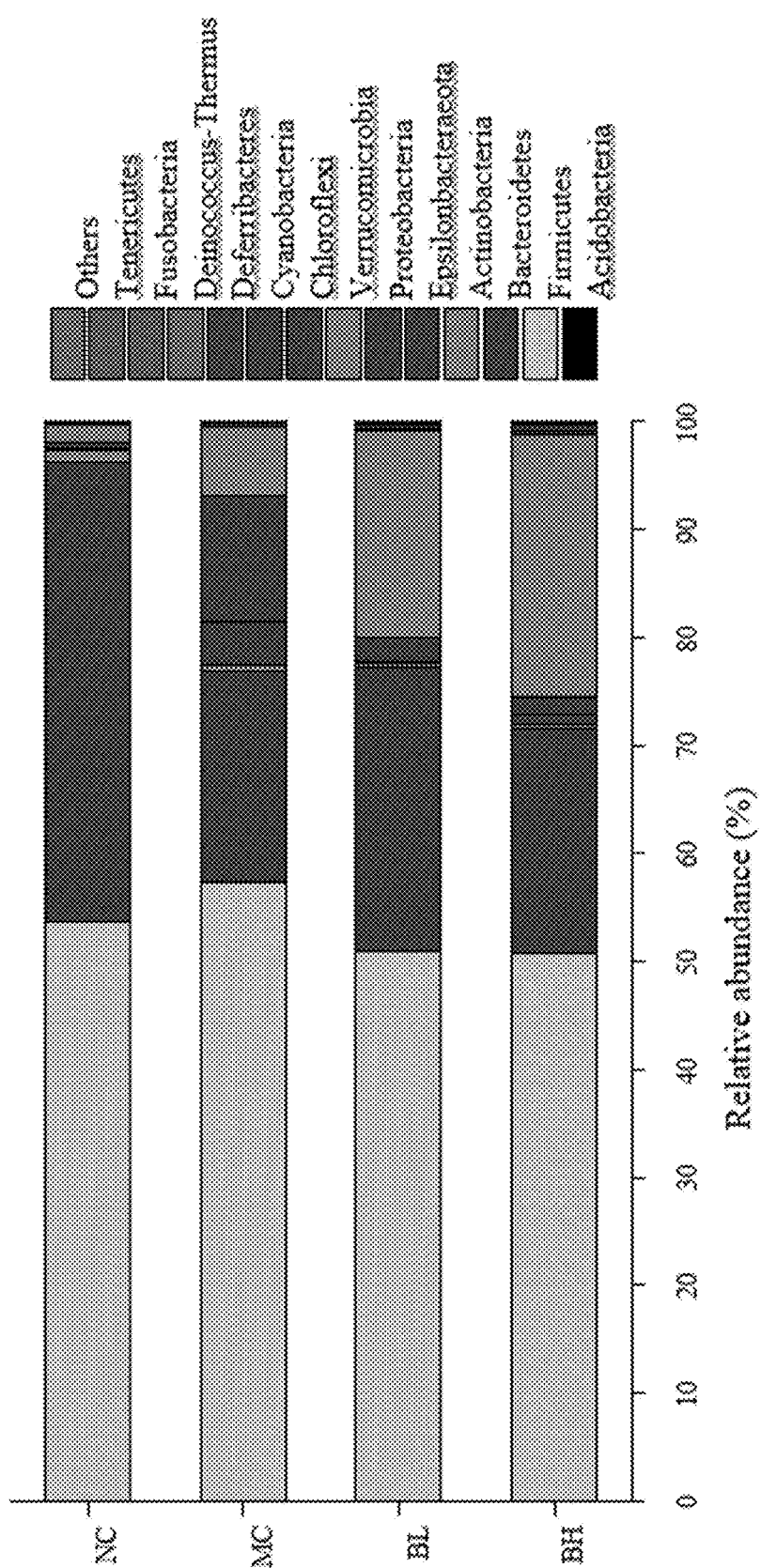
Figure 6D:
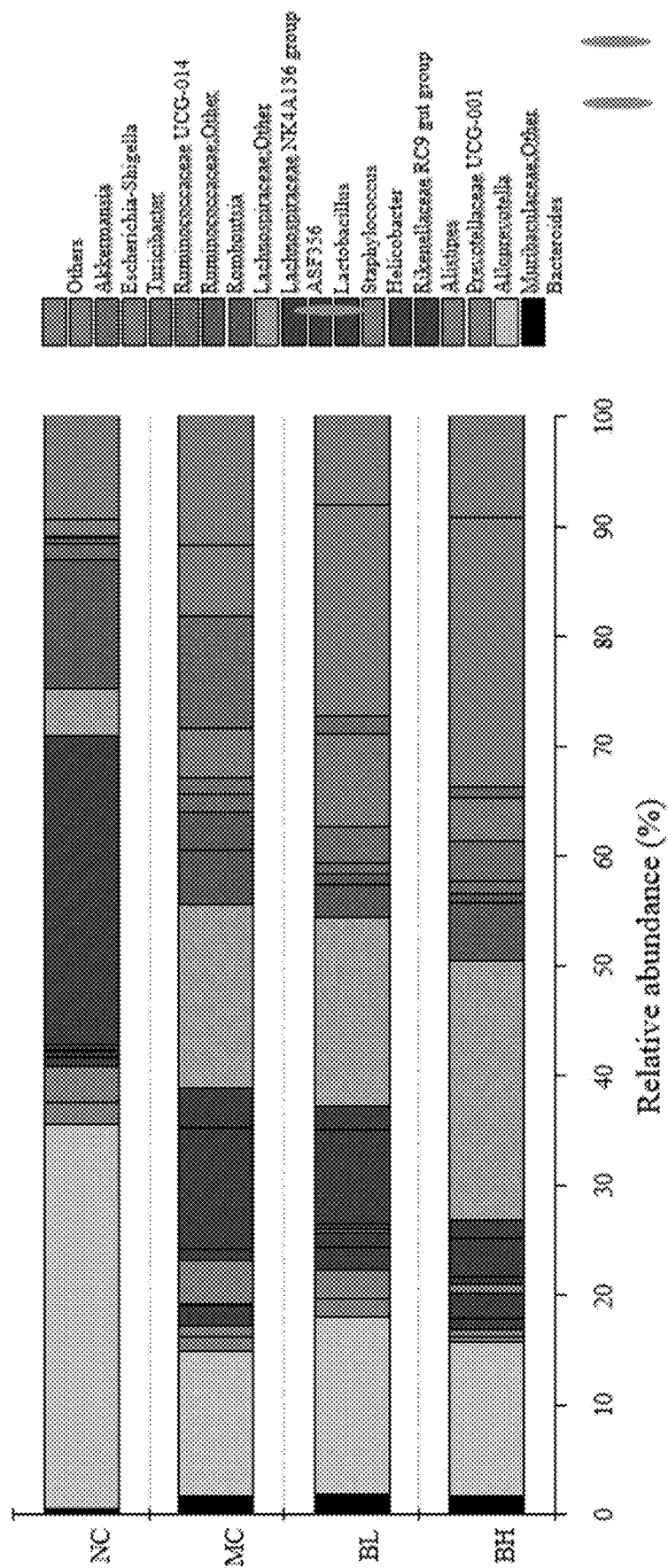

As shown in FIG. 6C, at a phylum level, a relative abundance of Bacteroidetes of mice in the model group was lower than that in the control group, and relative abundances of Firmicutes, *E. coli*, and Proteobacteria were increased. However, in the low-dose and high-dose groups, these changes were reversed to a similar level to the control group. In addition, compared with the model group, a relative abundance of Verrucomicrobia in the intervention measures with the two *B. lactis* strain XLTG11 doses was increased in a dose-dependent manner. As shown in FIG. 6D, relative abundances of *Shigella, Romboutsia*, ASF356, *Staphylococcus*, and *Helicobacter* in the model group at a genus level were higher than those in the control group. However, both the low-dose group and high-dose group reversed this trend to some extent. In addition, the low-dose and high-dose *B. lactis* increased the relative abundances of Muribaculaceae, Ruminococcaceae UCG-014, Lachnospiraceae NK4A136 group, and Akkermansia, and compared with the model group, only the high-dose *B. lactis* strain XLTG11 reduced a relative abundance of Prevotellaceae. In particular, relative abundances of Alistipes and Turicibacter were significantly increased in the model group compared with the control group, and this trend was alleviated only in the high-dose group. Interestingly, both the low-dose and high-dose *B. lactis* strain XLTG11 reduced a *Lactobacillus* level.

Figure 7:
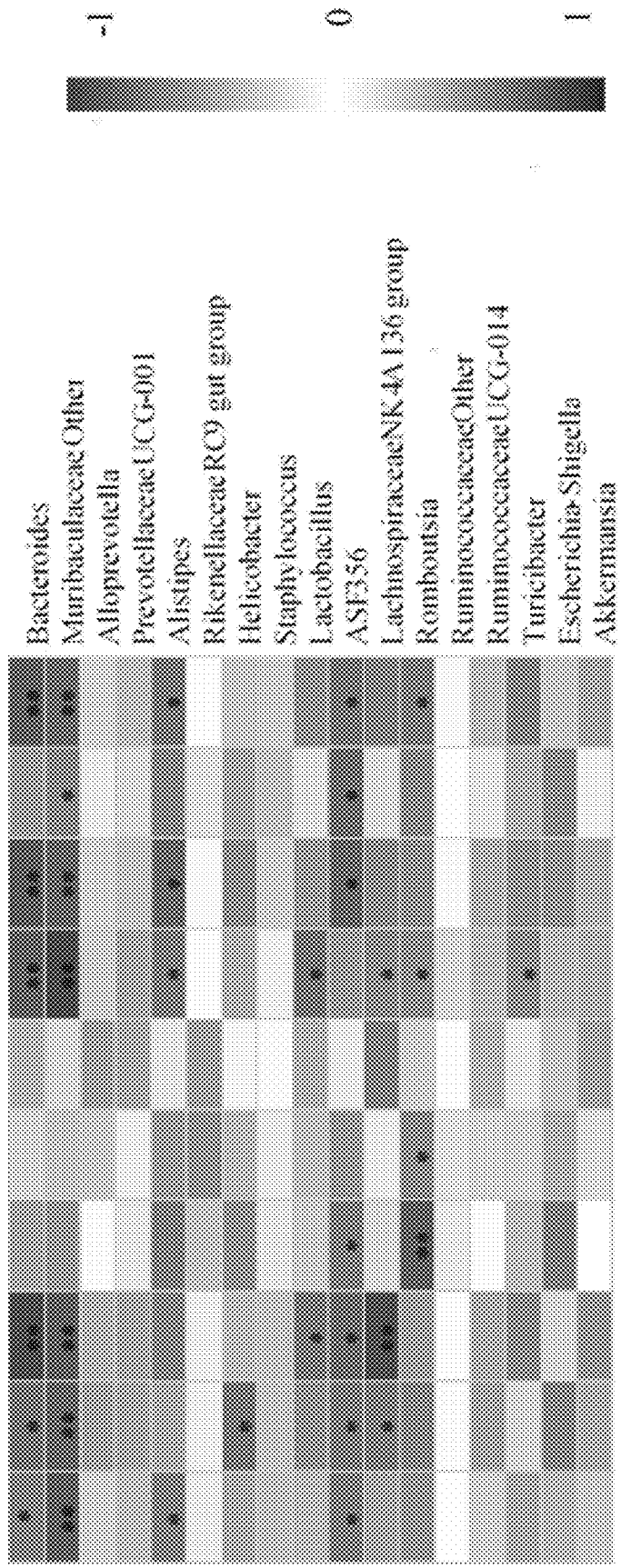
FIG. 7 shows the Spearman's correlation analysis of UC-associated symptoms and related gene expression with a dominant intestinal flora, where * and ** indicate significant correlations ($P<0.05$ and $P<0.01$, respectively).

In order to determine a role of an intestinal flora in reducing inflammatory biomarkers, correlations of the UC-associated symptoms and related gene expression with a dominant intestinal flora were analyzed at a genus level in this study. As shown in FIG. 7, a relative abundance of Bacteroidetes was significantly positively correlated with IL-1β, TNF-α, TLR4, and NF-κB, and was significantly negatively correlated with IL-10 and ZO-1. A relative abundance of the unclassified Muribaculaceae was positively correlated with IL-10 and ZO-1, but was negatively correlated with IL-1β, TNF-α, TLR4, MYD88, and NF-κB. The IL-10 and ZO-1 levels were significantly negatively correlated with Alistipes, and were significantly positively correlated with TLR4 and NF-κB. A relative abundance of Helicobacter was positively correlated with IL-1β. A relative abundance of Lactobacillus was significantly negatively correlated with TNF-α, and was significantly positively correlated with ZO-1. A relative abundance of ASF356 was positively correlated with the proinflammatory cytokines (IL-1β, TNF-α, and IL-6) and TLR4/MYD88/NF-κB signaling pathway, and was negatively correlated with IL-10. A relative abundance of Lachnospiraceae NK4A136 was positively correlated with IL-1β and TNF-α, and was negatively correlated with ZO-1. A relative abundance of Romboutsia was positively correlated with IL-6 and NF-κB, and was negatively correlated with Claudin-1 and ZO-1. A relative abundance of Turicibacter was significantly negatively correlated with ZO-1.

Example 7 Establishment of an Immunosuppression Model

SPF BALB/c male mice that each were 6 to 8 weeks old and weighed 18 g to 22 g were provided by Liaoning Changsheng Biotechnology Co., Ltd., with animal license No.: SCXK (Liao) 2020-0001. The BALB/c mice were randomly divided into 7 groups, with 8 mice in each group. Mice in the blank group and model group were each orally gavaged with 0.4 mL of NS, mice in the positive control group were each orally gavaged with levamisole hydrochloride (LEV) (10 mg·kg$^{-1}$), and mice in the B. lactis strain XLTG11 dose groups were orally gavaged with 0.4 mL of B. lactis strain XLTG11 suspensions at doses of 1×10$^9$ cfu, 1×10$^8$ cfu, 1×10$^7$ cfu, and 1×10$^6$ cfu per mouse, respectively. The mice were orally gavaged continuously for 28 d, during which the mice could eat and drink freely. On day 23 and day 24 after the oral gavage, mice in the model group, positive control group, and B. lactis strain XLTG11 dose groups were intraperitoneally injected with CTX (40 mg·kg$^{-1}$), and mice in the blank group were intraperitoneally injected with an equal volume of NS.

Example 8 Determination of an Immune Organ Index

On day 28 after the oral gavage, mice in each group were weighed and then sacrificed by cervical dislocation, the thymus and spleen were collected and weighed, and the thymus and spleen indexes were calculated. Thymus or spleen index=thymus or spleen mass (mg)/mouse body mass (g).

Figure 8:
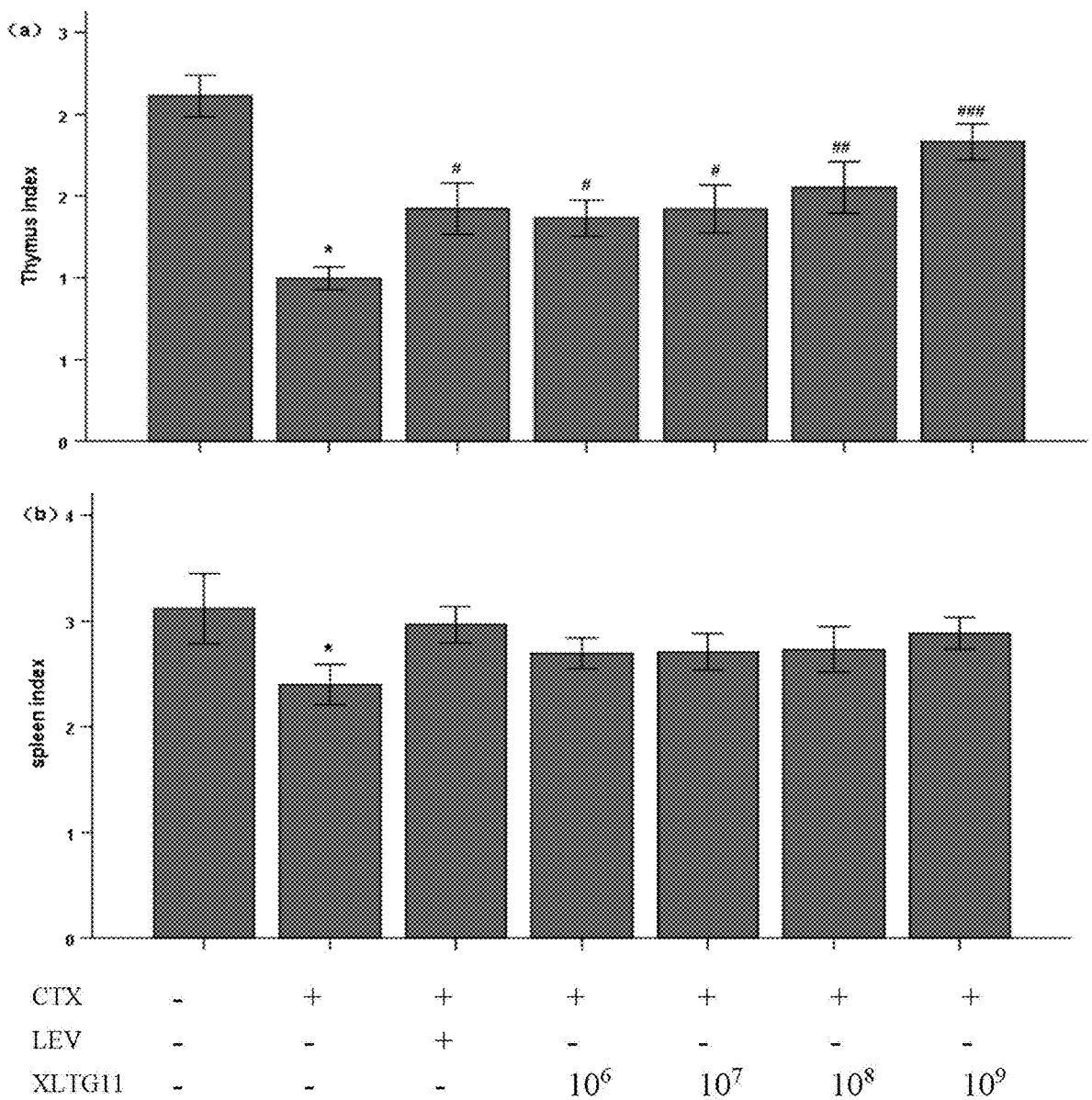
FIG. 8 shows the influence of different XLTG11 doses on the thymus index and spleen index of CTX mice, where *$P<0.05$ versus Control group; and #$P<0.05$, ##$P<0.01$, and ###$P<0.001$ versus Model group.

The effects of different B. lactis strain XLTG11 doses on the thymus and spleen indexes of CTX mice were shown in Table 1 and FIG. 8. Compared with the blank group, the thymus and spleen indexes of mice in the model group were significantly decreased (P<0.05). Compared with the model group, the thymus index of mice in the positive control group was increased (P<0.05) and the thymus index of mice in each B. lactis strain XLTG11 dose group was increased (P<0.05) in a dose-dependent manner.

TABLE 1

Effect of different B. lactis strain XLTG11 doses on thymus and spleen indexes of CTX mice (x̄ ± S, n = 8)

| Groups | Thymus index | Spleen index |
|---|---|---|
| Control | 2.11 ± 0.36 | 3.12 ± 0.94 |
| Model | 0.99 ± 0.20*** | 2.40 ± 0.54* |
| Positive control | 1.42 ± 0.44# | 2.97 ± 0.49 |
| XLTG11 (1 × 10$^6$ cfu) | 1.36 ± 0.31# | 2.69 ± 0.42 |
| XLTG11 (1 × 10$^7$ cfu) | 1.42 ± 0.41# | 2.71 ± 0.50 |
| XLTG11 (1 × 10$^8$ cfu) | 1.55 ± 0.44## | 2.73 ± 0.62 |
| XLTG11 (1 × 10$^9$ cfu) | 1.83 ± 0.32### | 2.89 ± 0.42 |

Note:
*P <0.05, and
***P <0.001 versus Control group; and
P <0.05,
P <0.01, and
P <0.001 versus Model group.

Example 9 Determination of Delayed Type Hypersensitivity (DTH)

On day 23 after the oral gavage, mice in each group were intraperitoneally injected with 0.2 mL of 2% (v/v) sheep red blood cells (SRBCs). On day 27 after the oral gavage, a thickness of a left hind toe was measured with a vernier caliper, each mouse was subcutaneously injected with 20 μL of 20% (V/V) SRBC at a measurement site, and 24 h later, a thickness of the left hind toe was measured once again. Multiple measurements were conducted at the same site, and an average was taken. A reaction degree of DTH was expressed by a difference in toe thickness before and after the injection.

The influence of different B. lactis strain XLTG11 doses on the toe thickness of CTX mice was shown in Table 2. Compared with the blank group, a toe thickness of mice in the model group was significantly decreased (P<0.05), and a toe thickness of mice in the B. lactis strain XLTG11 dose (1×10$^9$ cfu) group was significantly increased (P<0.05). Compared with the model group, a toe thickness of mice in the positive control group was increased significantly (P<0.01), and a toe thickness of mice in each B. lactis strain XLTG11 dose group was increased (P<0.05).

TABLE 2

Effect of different B. lactis strain XLTG11 doses on the toe thickness of CTX mice (x̄ ± S, n = 8)

| Groups | Toe thickness difference (cm) |
|---|---|
| Control | 0.050 ± 0.004 |
| Model | 0.034 ± 0.008* |
| Positive control | 0.054 ± 0.011## |
| XLTG11 (1 × 10$^6$ cfu) | 0.047 ± 0.012# |
| XLTG11 (1 × 10$^7$ cfu) | 0.051 ± 0.005# |
| XLTG11 (1 × 10$^8$ cfu) | 0.053 ± 0.009## |
| XLTG11 (1 × 10$^9$ cfu) | 0.066 ± 0.024*### |

Note:
*P <0.05 versus Control group; and
P <0.05,
P <0.01,
***P <0.001 versus Model group.

Example 10 Pathological Changes of Small Intestinal Mucosal Tissue

The mice were sacrificed by cervical dislocation, a small intestinal mucosal tissue was collected from mice in each group, fixed with 4% PFA, dehydrated, embedded, and sectioned to prepare paraffin sections, and the conventional HE staining was conducted. A pathological change of a small intestinal mucosal tissue was observed under an optical microscope.

Figure 9:
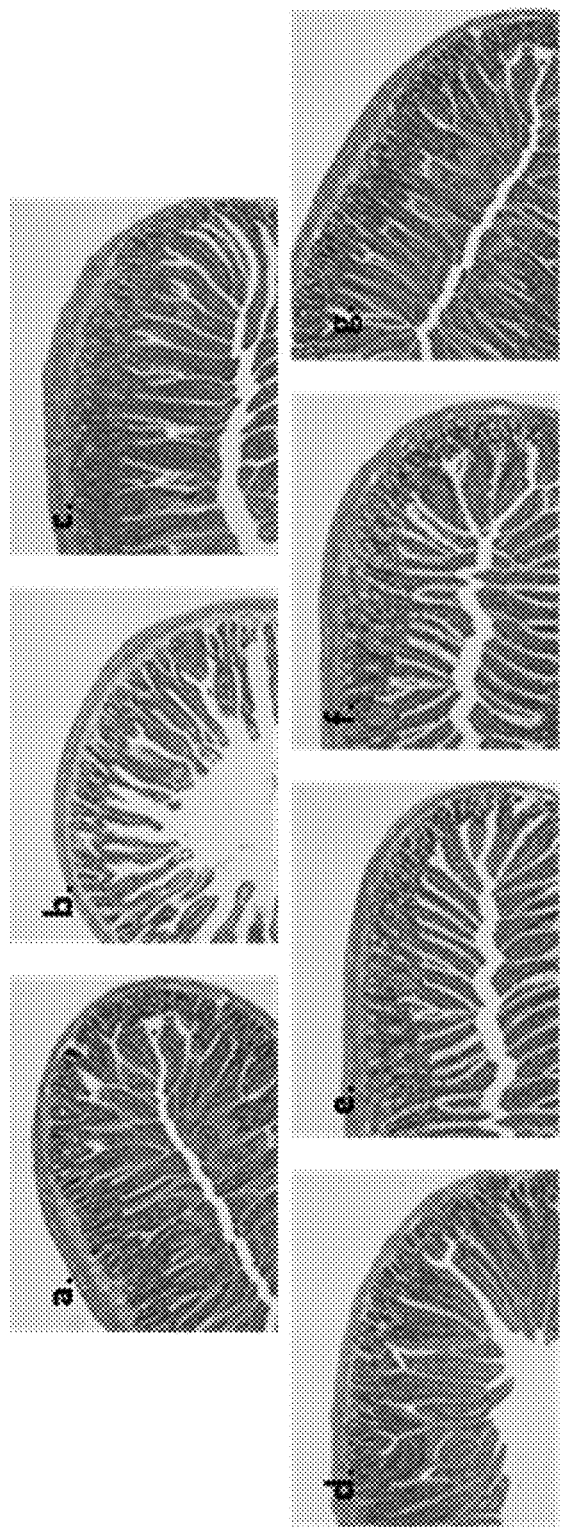
FIG. 9 shows the hematoxylin-eosin (HE) staining results of small intestinal mucosal tissues observed under an optical microscope (×100).

The HE staining results of mice in each group were shown in FIG. 9. The small intestinal mucosal tissues of mice in the blank group had a complete structure and neatly-arranged villi with uniform thickness. The small intestinal mucosal tissues of mice in the model group were damaged, and had a thinned intestinal wall and thinned villi that were different in length and sparsely arranged. In the positive control group and each *B. lactic* strain XLTG11 dose group, the damage of the small intestinal mucosal tissue was improved and the lesion degree of villi was alleviated. With the increase of the dose, the damage of the small intestinal mucosal tissue in mice was alleviated in a dose-dependent manner, and the *B. lactis* strain XLTG11 at $1 \times 10^9$ cfu exhibited the most significant effect.

Example 11 Determination of a Villus Height of a Small Intestinal Mucosa

The small intestinal mucosal tissue section of Example 10 was taken, a target area of the small intestinal tissue was selected and imaged at a magnification of 100×, the Image-Pro Plus 6.0 analysis software was used to determine heights of 5 intact intestinal villi (villus height) in each section with mm as a standard unit, and then an average was taken.

Figure 10:
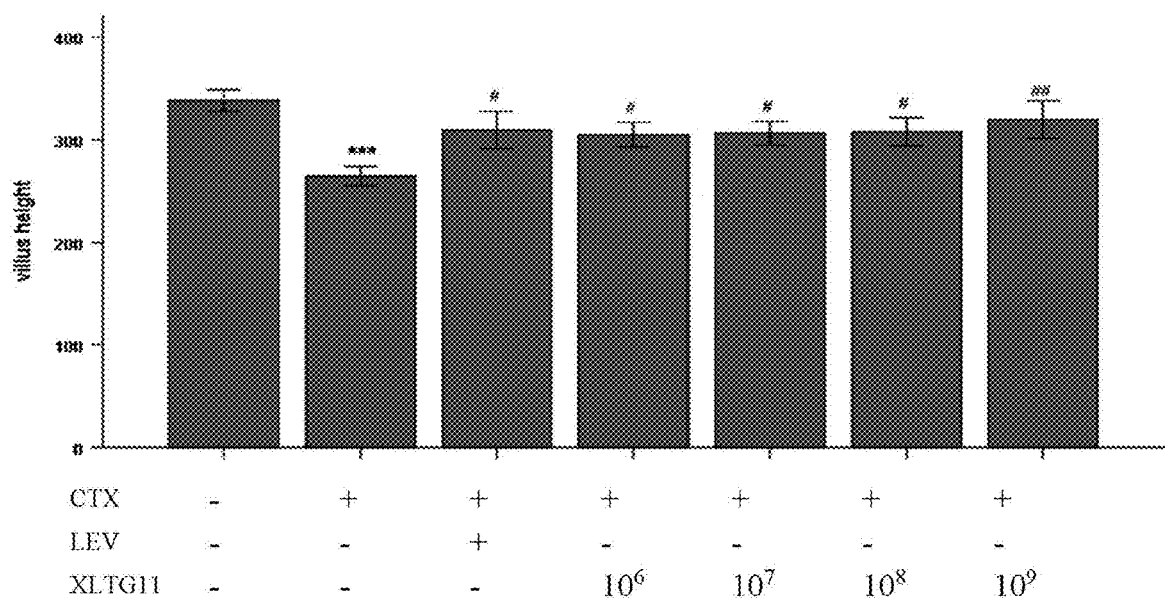
FIG. 10 shows the pathological changes (villus height) of small intestinal mucosal tissues, where *$P<0.05$ versus Control group; and #$P<0.05$, ##$P<0.01$, and ###$P<0.001$ versus Model group.

The villus height measurement results of small intestinal mucosas of mice in each group were shown in FIG. 10. Compared with the blank group, a small intestinal villus height of mice in the model group was significantly decreased (P<0.001). Compared with the model group, the small intestinal villus height of mice in the positive control group was increased (P<0.05), and the small intestinal villus height of mice in each *B. lactis* strain XLTG11 dose group was increased (P<0.05).

Example 12 Determination of the Number of Small Intestinal Goblet Cells

Sections were prepared by the same process as in Example 11. A section was stained with periodic acid Schiff (PAS), and the morphology and distribution of small intestinal intraepithelial goblet cells (goblet cell number) were observed under an optical microscope. A target area of the small intestinal tissue was selected and imaged at a magnification of 100×, the Image-Pro Plus 6.0 analysis software was used to determine the number of goblet cells on 5 intestinal villi in each section and a corresponding epithelial length with mm as a standard unit, and the number of goblet cells per unit length was calculated as follows: number of goblet cells/length.

Figure 11:
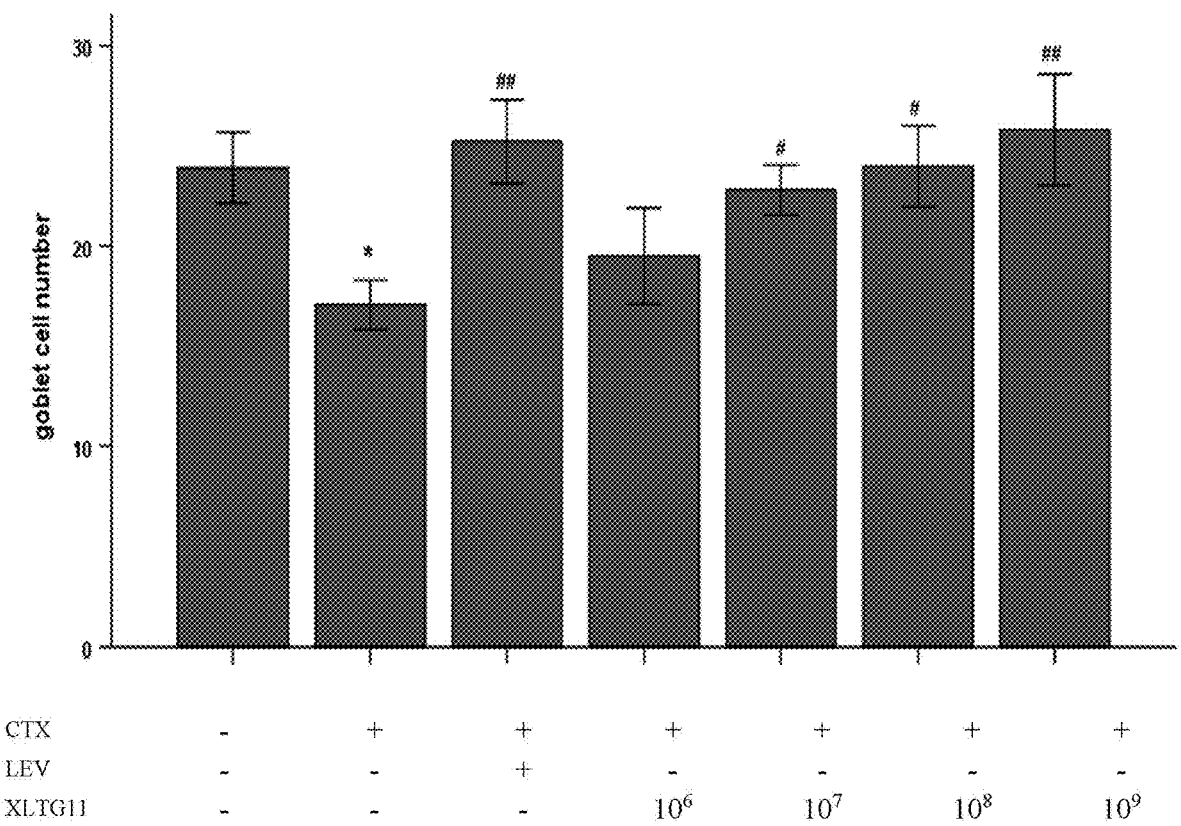
FIG. 11 shows the number of small intestinal goblet cells, where *$P<0.05$ versus Control group; and #$P<0.05$, ##$P<0.01$, and ###$P<0.001$ versus Model group.

The goblet cell number results of mice in each group were shown in Table 3 and FIG. 11. Compared with the blank group, the goblet cell number of mice in the model group was decreased (P<0.05). Compared with the model group, the goblet cell number of mice in the positive control group was significantly increased (P<0.01) and the goblet cell number of mice in each *B. lactis* strain XLTG11 dose group was increased (P<0.05).

TABLE 3

Small intestinal goblet cell number (x ± S, n = 8)

| Groups | Goblet cell number |
|---|---|
| Control | 23.90 ± 5.01 |
| Model | 17.06 ± 3.49* |
| Positive control | 25.22 ± 5.93## |
| XLTG11 (1 × $10^6$ cfu) | 19.50 ± 6.77 |
| XLTG11 (1 × $10^7$ cfu) | 22.79 ± 3.53# |
| XLTG11 (1 × $10^8$ cfu) | 23.96 ± 5.68# |
| XLTG11 (1 × $10^9$ cfu) | 25.80 ± 7.90## |

Note:
*P <0.05 versus Control group; and
P <0.05, and
P <0.01 versus Model group.

Example 13 Determination of a Cytokine Level in Serum min after the last oral gavage to mice in each group, eyeballs were removed, the whole blood was collected and centrifuged at 3000 r·min$^{-1}$ for 10 min, and the resulting serum was collected, dispensed, and frozen in a −80° C. refrigerator for test. Serum IgA, IgG, IL-2, IL-6, IFN-γ, and TNF-α levels were determined with an ELISA kit, and specific operation steps were conducted according to the instructions.

Figure 12:
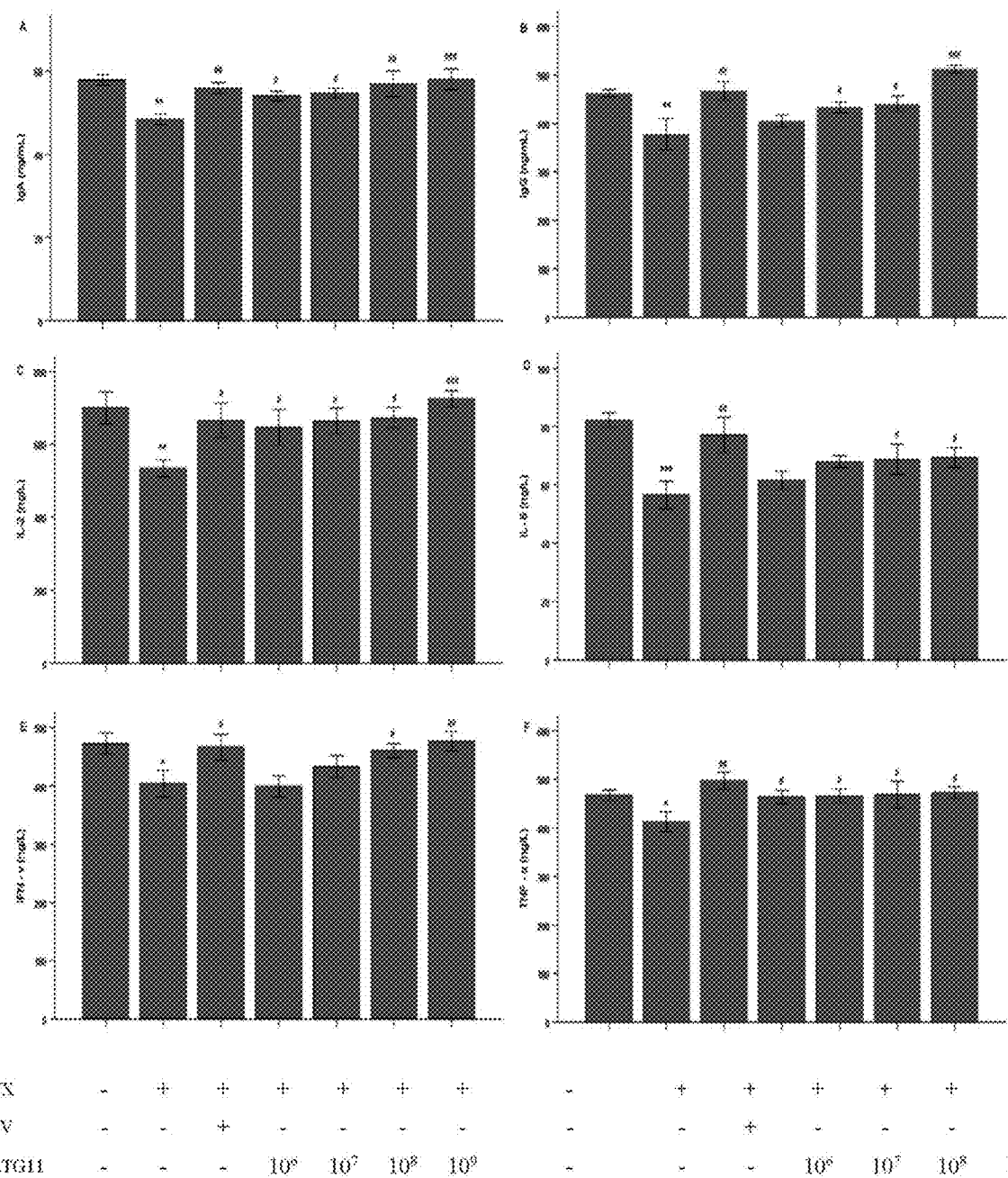
FIG. 12 shows the serum IgA, IgG, IL-2, IL-6, IFN-γ, and TNF-α levels in mice of each group, where *$P<0.05$ versus Control group; and #$P<0.05$, ##$P<0.01$, and ###$P<0.001$ versus Model group.

The test results of cytokines in serum of mice in each group were shown in Table 4 and FIG. 12. Compared with the blank group, the serum IgA, IgG, IL-2, IL-6, IFN-γ, and TNF-α levels of mice in the model group were decreased (P<0.05). Compared with the model group, the serum IgA, IgG, IL-2, IL-6, IFN-γ, and TNF-α levels of mice in the positive control group were increased (P<0.05); the IgA, IgG, IL-2, IL-6, IFN-γ, and TNF-α levels of mice in experimental groups 1 and 2 were increased (P<0.05); the IgA, IgG, IL-2, and TNF-α levels of mice in experimental group 3 (*B. lactis* strain XLTG11, 1×$10^6$ cfu) were increased (P<0.05); and the IgA, IL-2, and TNF-α levels of mice in experimental group 4 were increased (P<0.05).

TABLE 4

Serum IgA, IgG, IL-2, IL-6, IFN-γ, and TNF-α levels of mice in each group (x ± S, n = 8)

| Groups | IgA(ng · mL$^{-1}$) | IgG(ng · mL$^{-1}$) | IL-2(ng · L$^{-1}$) | IL-6(pg · mL$^{-1}$) | IFN-γ(ng · L$^{-1}$) | TNF-α(ng · L$^{-1}$) |
|---|---|---|---|---|---|---|
| Control | 57.87 ± 3.64 | 462.19 ± 21.64 | 700.68 ± 123.49 | 82.29 ± 7.06 | 472.73 ± 51.55 | 467.16 ± 30.28 |
| Model | 48.38 ± 3.65** | 378.10 ± 92.63** | 533.40 ± 65.94** | 56.50 ± 13.29*** | 403.99 ± 64.51* | 412.70 ± 57.50* |
| Positive control | 55.95 ± 3.66## | 467.59 ± 54.35## | 666.32 ± 134.02# | 77.12 ± 17.49## | 466.78 ± 62.60# | 496.86 ± 49.31## |
| XLTG11 (1 × $10^6$ cfu) | 54.11 ± 3.19# | 405.24 ± 35.33 | 646.22 ± 142.10# | 61.59 ± 8.77 | 399.58 ± 51.32 | 463.58 ± 38.69# |
| XLTG11 (1 × $10^7$ cfu) | 54.75 ± 3.30# | 432.87 ± 32.42# | 663.80 ± 103.17# | 67.96 ± 5.73 | 433.15 ± 53.26 | 465.62 ± 41.08# |

TABLE 4-continued

Serum IgA, IgG, IL-2, IL-6, IFN-γ, and TNF-α levels of mice in each group
($\bar{x} \pm S$, n = 8)

| Groups | IgA(ng·mL$^{-1}$) | IgG(ng·mL$^{-1}$) | IL-2(ng·L$^{-1}$) | IL-6(pg·mL$^{-1}$) | IFN-γ(ng·L$^{-1}$) | TNF-α(ng·L$^{-1}$) |
|---|---|---|---|---|---|---|
| XLTG11 (1 × 10$^8$ cfu) | 56.95 ± 8.72## | 440.56 ± 47.27# | 673.12 ± 80.22# | 68.73 ± 14.61# | 460.97 ± 33.15# | 468.12 ± 78.39# |
| XLTG11 (1 × 10$^9$ cfu) | 58.07 ± 6.85### | 512.72 ± 21.05### | 725.08 ± 63.62### | 69.36 ± 9.44# | 476.94 ± 47.67## | 472.56 ± 33.93# |

Note:
*P < 0.05,
**P < 0.01,
***P < 0.001 versus Control group;
P < 0.05,
P < 0.01,
P < 0.001 versus Model group

What is claimed is:

1. A method for preventing and/or alleviating colitis, comprising administering to a subject a product comprising a *Bifidobacterium lactis* strain XLTG11 having an accession number of CGMCC No. 18738 in an effective amount.

2. The method according to claim 1, wherein the colitis is ulcerative colitis.

3. A method for modulating an intestinal flora, comprising administering to a subject a product comprising a *Bifidobacterium lactis* strain XLTG11 having an accession number of CGMCC No. 18738 in an effective amount.

4. A method for inhibiting an activation of a TLR4/MYD88/NF-κB signaling pathway, comprising administering to a subject a product comprising a *Bifidobacterium lactis* strain XLTG11 having an accession number of CGMCC No. 18738 in an effective amount.

5. A method for enhancing an immune function, comprising administering to a subject a product comprising a *Bifidobacterium lactis* strain XLTG11 having an accession number of CGMCC No. 18738 in an effective amount.

6. The method according to claim 1, wherein the *Bifidobacterium lactis* strain XLTG11 is administrated at a dosage of 1×10$^6$ cfu to 1×10$^9$ cfu.

7. The method according to claim 3, wherein the *Bifidobacterium lactis* strain XLTG11 is administrated at a dosage of 1×10$^6$ cfu to 1×10$^9$ cfu.

8. The method according to claim 4, wherein the *Bifidobacterium lactis* strain XLTG11 is administrated at a dosage of 1×10$^6$ cfu to 1×10$^9$ cfu.

9. The method according to claim 5, wherein the *Bifidobacterium lactis* strain XLTG11 is administrated at a dosage of 1×10$^6$ cfu to 1×10$^9$ cfu.

* * * * *